United States Patent [19]

Clark

[11] Patent Number: 4,638,014
[45] Date of Patent: Jan. 20, 1987

[54] ANTICONVULSANT METHOD AND FORMULATIONS
[75] Inventor: C. Randall Clark, Auburn, Ala.
[73] Assignee: Research Corporation, Tucson, Ariz.
[21] Appl. No.: 769,521
[22] Filed: Aug. 26, 1985
[51] Int. Cl.$^4$ .......................................... A61K 31/165
[52] U.S. Cl. ..................................................... 514/619
[58] Field of Search ........................................ 514/619
[56] References Cited
U.S. PATENT DOCUMENTS
4,004,029 1/1977 Collins ................................ 260/558

FOREIGN PATENT DOCUMENTS
1198019 7/1970 United Kingdom .

Primary Examiner—Stanley J. Friedman
Attorney, Agent, or Firm—Scully, Scott, Murphy & Presser

[57] ABSTRACT

This invention relates to certain aminobenzanilide compounds, and to the use, in the treatment of mammals, of certain aminobenzanilide compounds as anticonvulsant agents.

5 Claims, No Drawings

ANTICONVULSANT METHOD AND FORMULATIONS

BACKGROUND OF THE INVENTION

1. Field of the Invention

The present invention relates to anticonvulsant drugs, and processes for using such drugs, wherein the drugs are based on 3- and 4-amino-N(alkyl phenyl) benzamide compounds. The most preferred of such benzamide compounds for this utility is 4-amino-N-(2,6-dimethyl phenyl)-benzamide.

2. Description of the Prior Art

The several anticonvulsant drugs marketed to date in the United States provide significant seizure relief for only 50–75% of epileptic patients. The therapeutic effects are sometimes accompanied by serious side effects such as sedation, ataxia, psychoses, suicidal depression, gastrointestinal disturbances, gingival hyperplasia, lymphadenopathies, megaloblastic anemias, hepatotoxicity, nephropathies, hirsutism, and fetal malformations. These side effects, which range in severity from mild sedation to death from aplastic anemia, are particularly troublesome since most of the marketed anticonvulsants have very low therapeutic ratios. For example, phenytoin, one of the most widely used anticonvulsants, controls seizures in man only when plasma levels reach 10 mcg/ml. Toxic effects such as nystagmus are seen at around 20 mcg/ml, ataxia is obvious at 30 mcg/ml, and lethargy is apparent at about 40 mcg/ml. See in this regard "The Pharmacological Basis of Therapeutics" (Gilman, Goodman, and Gilman, ed., 6th Ed., MacMillan Publishing Co., Inc., New York, N.Y., (1980)), p. 455. In view of these facts, most epileptologists indicate there is a definite need for more selective and less toxic anticonvulsant drugs.

U.S. Pat. No. 4,379,165 which issued April 5, 1983 and J. Medicinal Chemistry, 1984, Vol. 27, pages 779 to 782 disclose the use as anti-convulsants of certain amino-benzamide compounds. Although these compounds have a useful level of anticonvulsant activity when compared to previously employed prototype antiepileptic drugs such as phenobarbitol, phenytoin, mephenytoin and carbamazepine, such levels of anticonvulsant activity require the use of relatively large doses of such materials to impart the desired level of such activity and thus increase the danger of causing undesired toxic side effects. The amino-benzamide compounds of these two publications are also of limited scope, structurally. For example, none of the phenyl or benzyl groups contain any ring substituents other than the amino group in the benzamide radical.

The compounds 4-amino-N-(2-methyl phenyl) benzamide, 4-amino-N-(4-methyl phenyl) benzamide and 4-amino-N-(2,6-dimethyl phenyl) benzamide, among others, and a process for their preparation, are disclosed by P. Grammaticakis in Compt. Rend., 259, (23), Page 4295 1965 and also in Chemical Abstracts 62:11732b(1965). No utility is disclosed for these compounds in these publications.

Chem. Abs., Vol. 75; 1971; 35466g and Chem. Abs, Vol. 76, 1972, 140260d disclose the preparation, and use as analgesics, antiinflammatory, antipyretic or antiphlosgistics, of certain selected 4-amino benzoic acid anilides.

Prior to the present invention it has not been possible to provide anticonvulsant drugs which would provide levels of anticonvulsant activity significantly better then the levels provided by phenytoin and carbamazepine which provide levels of antimaximal electroshock (MES) activity in mice of the order of about 8.81 to 9.50 MES ED$_{50}$ (mg/kg) when employing an intraperitoneal dosage.

The amino-benzamide compounds of U.S. Pat. No. 4,379,165 and of the J. Medicinal Chemistry publication, supra, provide activity levels in mice of the order of about 18 to 67 MES ED$_{50}$ (mg/kg) under the same test conditions.

An object of the present invention, therefore, is to provide, as a novel class of anticonvulsant drugs certain 3- and 4-amino (alkyl phenyl) benzamides, some of which have significantly improved levels of anticonvulsant activity as compared to the previously available anticonvulsant drugs.

A further object of the present invention is to provide anti-convulsant drugs which are relatively safe to use at dosage levels providing useful levels of anticonvulsant activity.

Another object of the present invention is to provide anticonvulsant drugs that may be effectively administered orally.

Another object of the present invention is to provide certain novel 3- and 4-amino (alkyl phenyl) benzamides which may be used as anticonvulsant drugs.

SUMMARY OF THE INVENTION

This invention provides a method for treating and preventing convulsions in mammals in need of such treatment which comprises administering to said mammal an effective amount of certain 3- or 4-amino-N-(alkyl phenyl) benzamides, as described more fully hereinafter, and in particular, 4-amino-N-(2,6-dimethylphenyl)-benzamide, or a pharmaceutically acceptable acid addition salt thereof. According to a further aspect of the present invention, there are provided pharmaceutical formulations which comprise as active ingredient, said benzamide compounds, and in particular 4-amino-N-(2,6-dimethylphenyl) benzamide, or a pharamceutically acceptable acid addition salt thereof, in association with a pharmaceutically acceptable carrier, diluent, or excipient.

DETAILED DESCRIPTION AND PREFERRED EMBODIMENT

The present invention thus relates to the use, as a drug for treating and preventing convulsions in mammals, of effective amounts for such purposes of a $$\text{3- or 4-amino-N-[(alkyl)}_n \text{ phenyl]benzamide} \quad \text{I}$$

wherein the alkyl groups in such compounds contain 1 to about 4 carbon atoms and n is 1 or 2. The alkyl groups which may be present in such compounds would include methyl, ethyl, propyl, isopropyl and butyl. These compounds may also be described as 3- or 4-aminobenzanilide compounds having the structure

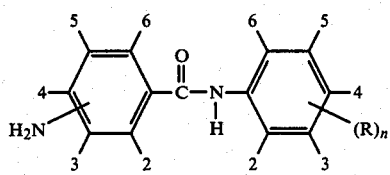

wherein R is a $C_1$ to $C_4$ alkyl group and is in 1 or 2.

It is believed that the following of such II structure compounds, shown in Table I below, which have been prepared and successfully evaluated as anticonvulsants as noted below, are compounds which are, it is believed, not disclosed to any extent in the prior art:

TABLE I

Compounds of Structure I Not Previously Disclosed

| Compound | Position of $H_2N$ Group* | Position of R or alkyl groups and hydrogen atoms** | | | | |
|---|---|---|---|---|---|---|
| | | 2 | 3 | 4 | 5 | 6 |
| II-1 | 3 | $CH_3$ | H | H | H | $CH_3$ |
| II-2 | 4 | H | $CH_3$ | H | H | H |
| II-3 | 4 | $CH_3$ | H | $CH_3$ | H | H |
| II-4 | 4 | H | $CH_3$ | $CH_3$ | H | H |
| II-5 | 4 | H | $CH_3$ | H | $CH_3$ | H |
| II-6 | 4 | $CH(CH_3)_2$ | H | H | H | H |
| II-7 | 4 | $CH(CH_3)_2$ | H | H | H | $CH_3$ |
| II-8 | 4 | $CH(CH_3)_2$ | H | H | H | $CH_2CH_3$ |

*in left hand phenyl ring of structure II (the hydrogen atoms in the unsubstituted positions of such ring are not shown.)
**in right hand phenyl ring of structure II.

The most preferred of the structure I compounds for use as an anticonvulsant is 4-amino-N-(2,6-dimethyl phenyl) benzamide.

The 3- and 4-aminobenzanilide compounds of the present invention may be prepared by procedures known to those in the art. Such procedures are disclosed in several of the prior art references noted above, i.e., P. Grammaticakis in Compt. Rend. 259 (23), Page 4295, 1965 and in Chem. Abs. 62:11732b (1965) as well as in Chem. Abs. 75:35466g (1971) and Chem. Abs. 76:140260d(1972). Such references disclose the preparation of some of the structure I compounds generally described above, including 4-amino-N-(2-methyl phenyl) benzamide, 4-amino-N-(4-methyl phenyl) benzamide and 4-amino-N-(2,6-dimethyl phenyl) benzamide. The undisclosed analogous compounds of Structure I or II can be prepared in a similar fashion, as by using the following general reaction Scheme I, wherein R and n are as defined above:

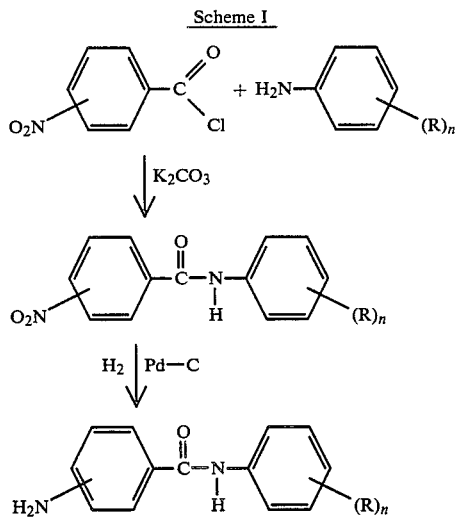

Scheme I

The benzamide compounds of the present invention can be used as such, as the drug, or in the form of a pharmaceutically effective acid addition salt thereof.

The pharmaceutically acceptable acid addition salts of this invention can be prepared by standard methods known in the art employing those acids of sufficient acidity to form acid addition salts with the basic aniline group of the benzamide compounds of this invention. These include salts derived from inorganic acids such as hydrochloric acid, nitric acid, phosphoric acid, sulfuric acid, hydrobromic acid, hydriodic acid, phosphorous acid and the like, as well as salts derived from organic acids such as aliphatic mono- and di-carboxylic acids, phenyl-substituted alkanoic acids, hydroxy-alkanoic and -alkanedioic acids, aromatic acids, aliphatic and aromatic sulfonic acids, etc. Such pharmaceutically acceptable salts thus include the sulfate, metaphosphate, pyrophosphate, chloride, bromide, iodide, fluoride, oxalate, maleate, benezene-sulfonate, toluenesulfonate, chlorobenzenesulfonate, methanesulfonate, propanesulfonate, naphthalene-1-sulfonate and naphthalene-2-sulfonate salts and the like. The preferred salts are those derived from inorganic acids, especially hydrochloric acid.

The benzamide compound of choice may be administered as an anticonvulsant agent by various routes including the oral, rectal, transdermal, subcutaneous, intravenous, intramuscular, or intranasal routes. It is usually employed in the form of a pharmaceutical composition. It is a special feature of this invention that this compound is effective as an anticonvulsant following oral administration. The invention includes a pharmaceutical composition comprising from about 1% to about 95% by weight of the benzamide compound, or a pharmaceutically acceptable acid addition salt thereof, associated with a pharmaceutically acceptable carrier.

In making the compositions of the present invention, the active ingredient will usually be mixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the composition can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compounds, soft and hard gelatin capsules, suppositories, sterile injectable solutions and sterile packaged powders.

Some examples of suitable carriers and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, methyl cellulose, methyl- and propyl-hydroxybenzoates, talc, magnesium stearate and mineral oil. The formulations can additionally include lubricating agents, wetting agents, emulsifying and suspending agents, preserving agents, sweetening agents or flavoring agents. The compositions of the invention may be formulated so as to provide quick, sustained or delayed release of the active ingredient after administration to the patient.

The compositions are preferably formulated in a unit dosage form, each dosage containing from about 5 to about 500 mg, more usually 25 to about 300 mg, of the active ingredient. The term "unit dosage form" refers to physically discrete units suitable as unitary dosages for human subjects and other mammals, each unit containing a predetermined quantity of active material calculated to produce the desired therapeutic effect, in association with the required pharmaceutical carrier.

The benzamide compound is effective over a wide dosage range. For example, dosages per day will normally fall within the range of about 0.5 to about 20 mg/kg of body weight. In the treatment of adult humans, the range of about 1 to 5 mg/kg, in single or divided doses, is preferred. However, it will be understood that the amount of the compound actually administered will be determined by a physician, in the light of the relevant circumstances including the condition to be treated, the chosen route of administration, the age, weight, and response of the individual patient, and the severity of the patient's symptoms, and the specific benzamide compound selected for use.

The following examples further illustrate the preparation of the benzamide compounds and formulations employed in this invention. The examples are illustrative only and are not intended to limit the scope of the invention in any way.

GENERAL EXPERIMENTAL

Melting points were determined in open glass capillaries using a Thomas-Hoover melting point apparatus and are uncorrected. IR spectra were recorded in chloroform solutions in matched sodium chloride cells or as fluorocarbon mulls using a Beckman 4230 spectrophotometer. All $^1$H NMR spectra were measured in CDCl$_3$ on a Varian T-60A spectrometer with an internal standard of tetramethylsilane. Elemental analyses (C,H,N) were performed by Atlantic Microlab Inc., Atlanta, Ga.

3- or 4-Nitrobenzanilides. A solution of the appropriate alkylaniline (0.03–0.07 mole) in 35 ml of tetrahydrofuran was added to 200 ml of 20% (w/v) aqueous potassium carbonate contained in a 1 L three-necked flask equipped with a magnetic stirrer, reflux condenser, addition funnel and a heating mantle. A solution of 3- or 4-nitrobenzoyl chloride (2 fold molar excess) in 35 ml of tetrahydrofuran was added dropwise and the resulting mixture refluxed for 12 hours and maintained at or above pH 8 during the reaction period. The solution was then cooled to room temperature and extracted with chloroform (3×100 ml). The extracts were combined, dried over magnesium sulfate and evaporated. The resulting residues were purified by recrystallization from a petroleum ether-benzene mixture.

3- or 4-aminobenzanilides. A solution of 5.0 g of the appropriate 3- or 4-nitrobenzanilide in tetrahydrofuran or absolute ethanol was added to a Paar hydrogenation bottle along with 250 mg of 5% Palladium on carbon. The mixture was subjected to low pressure hydrogenation (45 psi) for 3 hours and the contents of the bottle filtered through celite. The filtrate was evaporated and the resulting residue purified by recrystallization from benzene-petroleum ether mixtures or by column chromatography on silica gel (40 mesh) using a step-wise solvent gradient of petroleum ether (boiling range 30–60° C.) and diethylether.

EXAMPLE 1

4-Amino-N-(2,6-dimethylphenyl) benzamide

A. Preparation of 4-nitro-N-(2,6-dimethylphenyl)-benzamide

A solution of 0.09 moles of 2,6-dimethyl-aniline in 35 ml of tetrahydrofuran was added to 200 ml of 20% (w/v) aqueous potassium carbonate contained in a one liter flask. A solution of 20 g of p-nitrobenzoyl chloride in 35 ml of tetrahydrofuran was added dropwise. The resulting mixture was refluxed for 12 hours while the pH was maintained at or above pH 8. The solution was cooled to room temperature and extracted three times, each with 100 ml of chloroform. The extracts were combined, dried over magnesium sulfate, and evaporated in vacuo. The resulting residue was crystallized from petroleum ether/ benzene affording 15 g of the desired subtitle intermediate, m.p. 192–194. B. Preparation of 4-amino-N-(2,6-dimethylphenyl) benzamide.

A solution of 5.0 g of 4-nitro-N-(2,6-dimethylphenyl) benzamide in 250 ml of ethanol was added to a Paar hydrogenation bottle along with 250 mg of 5% palladium on carbon. The mixture was subjected to low pressure hydrogenation (45 psi) for three hours. The mixture was filtered through celite and the filtrate was evaporated in vacuo. The resulting residue was purified by (crystallization from benzene-petroleum ether) [column chromatography over silica gel using a step-wise solvent gradient of petroleum ether and diethyl ether]to provide 2.2 g of the desired title product, m.p. 212°–215° C.

Analysis for C$_{15}$H$_{16}$N$_2$O:
Calculated: C, 74.97; H, 6.71; N, 11.66;
Found: C, 74.77; H, 6.75; N, 11.60.

EXAMPLES 2-13

A series of twelve other 4-aminobenzanilides were prepared in a manner analogous to that used in Example 1 above. The intermediate 4-nitrobenzanilides were obtained from 4-nitrobenzoylchloride and the appropriate alkyl-aniline under Schotten-Baumann type conditions. See in this regard Sonntag, N.O.V., Chem. Rev., 1953, Vol. 52, page 237, the disclosure of which is hereby incorporated herein by reference. The resulting 4-nitrobenzanilides were crystalline solids showing carbonyl absorption in the infrared spectrum at approximately 1675cm$^{-1}$. The aromatic nitro-group was reduced by low-pressure catalytic hydrogenation and the physical properties of the resulting 4-aminobenzanilides are reported in Table II, with those of the compound of Example 1.

TABLE II

Physical Properties of 4-Aminobenzanilides.[a]

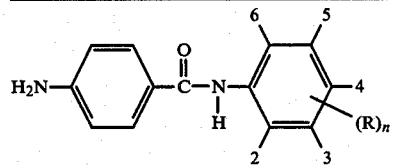

| Compound of Example | Position of R Groups & H Atoms | | | | | m.p.[c] | wave numbers cm$^{-1}$ | formula | Elemental Analyses, % | | | | | |
|---|---|---|---|---|---|---|---|---|---|---|---|---|---|---|
| | | | | | | | | | Theoretical | | | Found | | |
| | 2 | 3 | 4 | 5 | 6 | | | | C | H | H | C | H | N |
| 2 | H | H | H | H | H | 138–140 | 1660, 1620 | C$_{13}$H$_{12}$N$_2$O$_1$ | 73.56 | 5.70 | 13.20 | 73.47 | 5.78 | 13.16 |

TABLE II-continued

Physical Properties of 4-Aminobenzanilides.[a]

| Compound of Example | Position of R Groups & H Atoms | | | | | m.p.[c] | wave numbers cm$^{-1}$ | formula | Elemental Analyses, % | | | | | |
|---|---|---|---|---|---|---|---|---|---|---|---|---|---|---|
| | | | | | | | | | Theoretical | | | Found | | |
| | 2 | 3 | 4 | 5 | 6 | | | | C | H | H | C | H | N |
| 3 | CH$_3$ | H | H | H | H | 152–154 | 1660, 1620 | C$_{14}$H$_{14}$N$_2$O$_1$ | 74.31 | 6.24 | 12.38 | 74.21 | 6.24 | 12.37 |
| 4 | H | CH$_3$ | H | H | H | 114–116 | 1660, 1620 | C$_{14}$H$_{14}$N$_2$O$_1$ | 74.31 | 6.24 | 12.38 | 74.18 | 6.25 | 12.34 |
| 5 | H | H | CH$_3$ | H | H | 166–168 | 1660, 1620 | C$_{14}$H$_{14}$N$_2$O$_1$ | 74.31 | 6.24 | 12.38 | 74.23 | 6.24 | 12.34 |
| 6 | CH$_3$ | CH$_3$ | H | H | H | 165–167 | 1660, 1620 | C$_{15}$H$_{16}$N$_2$O$_1$ | 74.97 | 6.71 | 11.66 | 74.81 | 6.75 | 11.59 |
| 7 | CH$_3$ | H | CH$_3$ | H | H | 188–191 | 1660, 1620 | C$_{15}$H$_{16}$N$_2$O$_1$ | 74.97 | 6.71 | 11.66 | 74.93 | 6.73 | 11.62 |
| 8 | CH$_3$ | H | H | CH$_3$ | H | 190–192 | 1660, 1620 | C$_{15}$H$_{16}$N$_2$O$_1$ | 74.97 | 6.71 | 11.66 | 74.80 | 6.79 | 11.61 |
| 1 | CH$_3$ | H | H | H | CH$_3$ | 212–215 | 1655, 1620 | C$_{15}$H$_{16}$N$_2$O$_1$ | 74.97 | 6.71 | 11.66 | 74.77 | 6.75 | 11.60 |
| 9 | H | CH$_3$ | CH$_3$ | H | H | 120–122 | 1660, 1620 | C$_{15}$H$_{16}$N$_2$O$_1$ | 74.97 | 6.71 | 11.66 | 75.04 | 6.77 | 11.62 |
| 10 | H | CH$_3$ | H | CH$_3$ | H | 142–145 | 1660, 1620 | C$_{15}$H$_{16}$N$_2$O$_1$ | 74.97 | 6.71 | 11.66 | 74.86 | 6.76 | 11.64 |
| 11 | CH(CH$_3$)$_2$ | H | H | H | H | 174–176 | 1660, 1620 | C$_{16}$H$_{18}$N$_2$O$_1$ | 75.56 | 7.13 | 11.02 | 75.28 | 7.19 | 10.98 |
| 12 | CH(CH$_3$)$_2$ | H | H | H | CH$_3$ | 205–208 | 1655, 1620 | C$_{17}$H$_{20}$N$_2$O$_1$ | 76.08 | 7.51 | 10.44 | 75.96 | 7.55 | 10.39 |
| 13 | CH(CH$_3$)$_2$ | H | H | H | —CH$_2$CH$_3$ | 189–191 | 1660, 1620 | C$_{18}$H$_{22}$N$_2$O$_1$ | 76.56 | 7.85 | 9.92 | 77.48 | 7.56 | 9.46 |

[a]The infrared and nuclear magnetic resonance ($^1$H) spectra were consistent with structural assignments.

The results of the initial anticonvulsant and toxicity evaluation of the 4-aminobenzanilide compounds of Examples 1–13 are reported in Table III below. The preliminary screening was done at doses of the test compounds from 30 mg/kg up to 600 mg/kg administered ip in mice and evaluated against maximal electroshock seizures (MES) and subcutaneous Metrazole (scMet) induced convulsions and in the rotorod test for neurologic deficit. The intermediate 4-nitrobenzanilides were essentially inactive in the anticonvulsant tests.

TABLE III

Anticonvulsant Activity of 4-Aminobenzanilides of Examples 1–13

| Compound of Example | MES[a] | | scMet[a] | | Toxicity[a,b] | |
|---|---|---|---|---|---|---|
| | 30 min | 4 hrs | 30 min | 4 hrs | 30 min | 4 hrs |
| 2 | ++++ | ++ | +++ | — | +++ | ++ |
| 3 | ++++ | +++ | [c] | [c] | ++++[d] | ++ |
| 4 | +++ | ++ | ++ | — | ++ | + |
| 5 | +++ | +++ | ++++ | — | +++ | + |
| 6 | ++++ | ++ | +++ | [c] | +++[e] | [e] |
| 7 | ++ | + | + | — | + | — |
| 8 | ++ | — | ++ | — | — | — |
| 1 | ++++ | ++++ | [c] | [c] | ++++ | +++ |
| 9 | +++ | +++ | ++ | ++ | +++ | + |
| 10 | ++ | + | — | — | — | — |
| 11 | +++ | + | + | — | + | — |
| 12 | ++++ | ++ | — | — | — | — |
| 13 | ++++ | +++ | ++ | — | ++++[e] | +++ |

[a]++++, +++, ++ and + signify activity at 30, 100, 300 and 600 mg/kg, respectively; — denotes no activity observed at 600 mg/kg.
[b]determined by the rotorod test
[c]no activity at 300 mg/kg
[d]loss of righting reflex at 100 mg/kg; LD50 less than 600 mg/kg
[e]loss of righting reflex at 300 mg/kg; LD50 less than 600 mg/kg Previous studies by Clark et al., J. Med. Chem., 1984, Vol. 27, page 779 have demonstrated the high level of anticonvulsant activity associated with 4-aminobenzamides having aromatic and arylalkyl-groups substituted at the amide-nitrogen. The compound of Example 2 was observed, in such studies, to possess activity against MES and scMet induced convulsions in the 50 mg/kg dose range. Table III shows the anticonvulsant effects of substitution of additional alkyl groups on the aromatic ring. The compounds of Examples 1–13 all showed activity against MES induced convulsions at 300 mg/kg 30-minutes after administration with most compounds maintaining at least minimal anti-MES activity 4 hours after administration. Several compounds showed some activity against scMet induced convulsions at 30 minutes, however, the activity had essentially disappeared at 4 hours. Each of the monomethylated anilides of Examples 3 to 5 exhibited anticonvulsant activity similar to that of compound 2. Only compound 4 showed any appreciable difference between the dosages producing toxicity and anti-MES activity.

The compounds of Examples 6, 7, 8, 1, 9 and 10 represent all the possible dimethylated anilides and these compounds continue to show good anti-MES activity with compounds 6 and 1 effective at 30 mg/kg. Compound 6 gave anti-MES activity in approximately half the animals tested at 30 mg/kg. Initial evaluation of compound 1 gave an indication of the high level of anticonvulsant activity associated with this compound. Thirty minutes after administration, the compound of Example 1 exhibited anti-MES activity and rotorod toxicity at 30 mg/kg in all animals. Four hours after administration, the compound of Example 1 continued to exhibit anti-MES activity at 30 mg/kg with rotorod toxicity dropping to 100 mg/kg. No anti-scMet activity was observed at either 30 minutes or 4 hours. The testing was repeated for compound 1 using doses of 5, 10, 20 and 30 mg/kg and each group of 4 animals subjected to the rotorod and MES tests 30 minutes after administration. Rotorod toxicity was observed in 3 of 4 mice given 20 mg/kg and anti-MES activity in 4 of 4 mice given 5 mg/kg of the test substance. Thus, the initial profile of anticonvulsant activity for the compound of Example 1 was characterized by marked ability to modify the maximal electroshock seizure pattern and inability to elevate the Metrazol seizure threshold.

The remaining three compounds 11–13 all possess an ortho-isopropyl group and present diverse activity and toxicity profiles. The compounds show excellent anti-MES activity with compounds 12 and 13 appearing to be more potent that compound 11. However, compounds 11 and 12 show similar toxicity profiles in these preliminary studies. In contrast, compound 12 produced no rotorod toxicity in mice at a dose of 600 mg/kg while compound 13 showed toxicity in 1 out of 4 animals given 30 mg/kg. All animals (4 of 4) dosed with compound 13 at 300 mg/kg showed loss of righting reflex. This drastic difference in toxicity between compounds 12 and 13 is somewhat surprising considering the structural similarity of these two compounds.

From the initial screening results, several of the 4-aminobenzanilide compounds were selected for quantitation of anticonvulsant and toxic effect. The results of these evaluations are given in Table IV below.

indicated a significant degree of anti-MES activity for the compound of Example 1.

Continued studies at lower dosing levels successfully identified the anti-MES ED50 for the compound of Example 1 at 2.6 mg/kg and the ED50 at 15.01 mg/kg. The compound of Example 1 is the most potent amide of PABA observed thus far in these studies. The activity of the compound of Example 1 should be compared to that of compound 14 identified in the report of Clark et al., J. Med. Chem., 1984, Vol. 27, page 779 for its significant anti-MES activity. Compound 14 when administered ip in mice shows a TD50=170.78 and anti-MES ED50=18.02. Thus, the compound of Example 1

TABLE IV

| Compound of Example | Quantitative Anticonvulsant Activity of Selected 4-Aminobenzanilides | | | | |
|---|---|---|---|---|---|
| | TD50$^{a,b}$ | MES | | scMET | |
| | | ED50$^b$ | PI$^c$ | ED50$^b$ | PI$^c$ |
| 2 | 111.30 (98.01–127.65)$^d$ | 50.54 (40.81–59.43)$^d$ | 2.20 | 59.11 (32.85–102.81)$^d$ | 1.88 |
| 4 | 142.51 (130.89–161.13) | 46.96 (39.77–53.41) | 3.03 | 87.91 (62.25–111.23) | 1.62 |
| 6 | 103.90 (88.85–119.90) | 25.25 (12.50–31.75) | 4.11 | | |
| 1 | 15.01 (13.27–16.88) | 2.60 (2.18–3.07) | 5.77 | | |
| 9 | 194.14 (156.61–251.07) | 42.31 (38.02–50.30) | 4.59 | 80.84 (46.85–125.93) | 2.40 |
| 11 | 708.98 (556.77–815.69) | 81.52 (56.16–105.53) | 8.70 | | |
| 12 | >1500.0 | 86.13 (66.58–109.74) | >17.42 | | |
| 13 | 49.10 (40.62–57.10) | 16.67 (14.70–19.13) | 2.95 | | |
| 14 (Clark et al) | 170.78 (153.02–189.96) | 18.02 (13.41–21.43) | 9.50 | 41.78 (38.83–46.00) | 4.10 |
| Phenobarbital | 69.01 (62.84–72.89) | 21.78 (14.99–25.52) | 3.17 | 13.17 (5.87–15.95) | 5.24 |
| Phenytoin | 65.46 (52.49–72.11) | 9.50 (8.13–10.44) | 6.89 | | |
| Valproic Acid | 424.84 (368.91–450.40) | 271.66 (246.97–337.89) | 1.57 | 148.59 (122.64–177.02) | 2.87 |

$^a$Rotorod Procedure.
$^b$Doses reported are in milligrams per kilogram.
$^c$PI = protective index = TD50/ED50.
$^d$95% confidence limits.

With respect to the test results reported in Table IV it is to be noted that the ED50 values were determined against MES and scMet induced convlusion, and the TD50 values were measured by the rotorod procedure. Quantitative data were obtained against MES induced convulsions for all compounds, however, ED50s against scMet were obtained only for the compounds of Examples 2, 4 and 9. Compound 9 is the only one of the group whose anti-scMet activity produces a PI value (PI=TD50/ED50) greater than 2. The selectivity of effect against scMet is quite low for all three compounds as indicated by the rather low values for the slope (m) of the dose-response regression line for each compound. For example, compound 9 has m=3.02 for anti sc-Met activity which can be compared to m=12.0 for anti-MES in the same compound.

A comparison of the anti-MES ED50 values and the TD50 values in Table IV show the meta-toluidine derivative, the compound of Example 4, to have a similar activity profile to that for the parent aniline derivative, the compound of Example 2. The compound of Example 1 is the most potent and most toxic of the dimethylanilines examined. However, the compounds of Examples 6, 1 and 9 all show higher PI values than the parent compound, that of Example 2. As previously discussed the initial anticonvulsant screening studies shows an approximate 10-fold increase in toxicity and anti-MES activity in mice over compound 14. However, compound 14 has anti-scMet activity (ED50=41.78 mg/kg) which is absent in the compound of Example 1. Compound 14 has the structure:

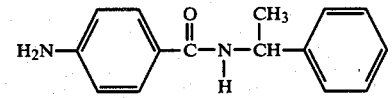

The ortho-isopropyl derivatives of the present invention, the compounds of Examples 11 and 12, have the highest PI values of any compounds examined in this study. This is the case even with the higher anti-MES ED50 values. The reason for the high PI values in these two compounds appears to be the extremely high TD50 values, especially for compound 12. The toxicity evaluation of compound 12 places the TD50 value at between 1500 and 2000 mg/kg. The drastic increase in toxicity observed between these compounds 12 and 13 as the 6-substituant of the aniline ring is altered from methyl to ethyl is unexpected.

The quantitative anticonvulsant data for the 4-aminobenzanilides in Table IV (especially that for compound 1) can be compared to that for the anticonvulsant drugs phenobarbital, phenytoin and valproic acid. The test for these drugs were conducted in the same assay procedure. The results indicate that this compound 1 possesses greater potency than any of the prototype anticonvulsants while showing a similar PI value. In most cases the slope of the regression lines for toxicity and activity are not parallel, and the PI is valid only at the dose-50 response. Thus, it is important to note the effect of slope by comparing the safety ratios (SR=TD3/ED97) for these compouds. In the MES test compound 1 gave an SR of 1.6 which can be compared to SR=2.3 for phenobarbital; SR=3.6 for phenytoin and SR=0.9 for vaproic acid. Compound 14 by comparison give an SR=3.5 in the same anti-MES test. The time of peak effect for toxicity and anti-MES activity was determined to be 30 minutes for compound 1.

The general toxicity profile for compound 1 was developed in mice by ip administration of the TD50, 2×TD50, and 4×TD50 doses. The toxicity induced by the TD50 dose was characterized by decreased motor activity, spasticity, ataxia, rotorod toxicity and sedation. All of these symptoms had disappeared after 2 hours and the animals appeared normal. Higher dosed produced muscle relaxation, loss of righting reflex, decreased respiration with cyanosis and ptosis in addition to the other symptoms. The animals appeared normal after 8 hours. The hypnotic dose (HD50) and lethal dose (LD50) for compound 1 were determined to be 43.80 and 160.83 mg/kg respectively. These values are significantly lower than those for phenobarbital (135.45 and 264.70 mg/kg), phenytoin (178.34 and 22.961 mg/kg), valproic acid (885.53 and 1104.62 mg/kg), and compound 14 (461.76 and 718.18).

The anticonvulsant activity profile for compound 1 was examined in a series of chemically induced seizures in mice. Compound 1 was ineffective against convulsions induced by sc metrazole, sc bicuculline, sc picrotoxin and sc strychnine even at doses up to 30 mg/kg. Bicuculline and picrotoxin (Krogsgaard-Larsen, P., J. Med. Chem., 1981, Vol. 24, page 1377) induce convulsions via a GABA antagonistic effect and strychnine blocks postsynaptic inhibition mediated by glycine (Krall et al, Epilepsia, 1978, Vol. 19, page 409). Thus, compound 1 is ineffective by all threshold tests and exhibits an activity profile similar to that of phenytoin.

Pharmacology. Initial anticonvulsant evaluation of compounds 1 to 13 was conducted using at least three dose levels (30, 100, 300 mg/kg) and in some cases a fourth dose of 600 mg/kg. All tests were performed using male Carworth Farms number-one mice. Test solutions of all compounds were prepared in 30% polyethylene glycol 400 and animals were dosed intraperitoneally (ip) at 30 minutes prior to testing.

Maximal electroshock seizures (MES) were elicited with a 60 cycle alternating current of 50mA intensity delivered for 0.2 second via corneal electrodes. A drop of 0.9% saline was instilled in the eye prior to application of electrodes. The animals were examined and evaluated immediately after the electroshock for the occurrence of clonic, flexor tonic, or extensor tonic convulsions or death. Abolition of the hind limb tonic extension component of the seizure was defined as protection in the MES test. The ED50 was determined for the test compound as the dose which inhibited the occurrence of hind limb tonic convulsions in one half of the animals immediately after the electroshock as determined by graphical interpolation.

The subcutaneous pentylenetetrazole (Metrazol) seizure threshold test (scMet) was conducted by administering 85 mg/kg of pentylenetetrazole as a 0.5% solution in the posterior midline. Protection in this test was defined as a failure to observe a single episode of clonic spasms of at least 5 second duration during a 30 minute period following administration of the test compound.

Neurological deficit was measured in mice using the rotorod test. The dosed animal was placed on a 1-inch diameter knurled plastic rod rotating at 6 rpm. Neurologic toxicity was defined as the failure of the animal to remain on the rod for 1 minute. The median anticonvulsant protency (ED50) and toxicity (TD50) were determined by the graphical method.

The following examples illustrate the use of the preferred anticonvulsant of the present invention, the compound of Example 1, 4-amino-N-(2,6-dimethylphenyl) benzanilide, in various drug composition forms in which it may be employed as an anticonvulsant.

EXAMPLE 15

Hard gelatin capsules are prepared using the following ingredients:

|  | Quantity (mg/capsule) |
| --- | --- |
| 4-Amino-N—(2,6-dimethyl-phenyl)benzamide sulfate | 250 |
| Starch dried | 200 |
| Magnesium stearate | 10 |

The above ingredients are mixed and filled into hard gelatin capsules in 460 mg quantities.

EXAMPLE 16

A tablet formula is prepared using the ingredients below:

|  | Quantity (mg/tablet) |
| --- | --- |
| 4-Amino-N—(2,6-dimethyl-phenyl) benzamide hydrobromide | 250 |
| Cellulose, microcrystalline | 400 |
| Silicon dioxide, fumed | 10 |
| Stearic acid | 5 |

The components are blended and compressed to form tablets each weighing 665 mg.

EXAMPLE 17

An aerosol solution is prepared containing the following components:

|  | Weight % |
| --- | --- |
| 4-Amino-N—(2,6-dimethyl-phenyl) benzamide hydrochloride | 0.25 |
| Ethanol | 29.75 |
| Propellant 22 (Chlorodifluoromethane) | 70.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

EXAMPLE 18

Tablets each containing 60 mg of active ingredient are made up as follows:

| | |
|---|---|
| 4-Amino-N—(2,6-dimethyl)-phenyl) benzamide | 60 mg |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

EXAMPLE 19

Capsules each containing 80 mg of medicament are made as follows:

| | |
|---|---|
| 4-Amino-N—(2,6-dimethyl-phenyl) benzamide | 80 mg |
| Starch | 59 mg |
| Microcrystalline Cellulose | 59 mg |
| Magnesium stearate | 2 mg |
| Total | 200 mg |

The active ingredient, cellulose, starch and magnesium stearate are blended, passed through a No. 45 mesh U.S. sieve, and filled into hard gelatin capsules in 200 mg quantities.

EXAMPLE 20

Suppositories each containing 225 mg of active ingredient are made as follows:

| | |
|---|---|
| 4-Amino-N—(2,6-dimethyl-phenyl) benzamide | 225 mg |
| Saturated fatty acid | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

EXAMPLE 21

Suspensions each containing 50 mg of medicament per 5 ml dose are made as follows:

| | |
|---|---|
| 4-Amino-N—(2,6-dimethyl-phenyl) benzamide hydrochloride | 50 mg |
| Sodium carboxymethyl cellulose | 50 mg |
| Syrup | 1.25 ml |
| Benzoic acid solution | 0.10 ml |
| Flavor | q.v. |
| Color | q.v. |
| Purified water to | 5 ml |

The medicament is passed through a No. 45 mesh U.S. sieve and mixed with the sodium carboxymethyl cellulose and syrup to form a smooth paste. The benzoic acid solution, flavor and color are diluted with some of the water and added, with stirring. Sufficient water is then added to produce the required volume.

EXAMPLE 22 a 3-amino compound of the present invention was also prepared and evaluated as an anticonvulsant. The compound was 3-amino-N-(2,6-dimethyl phenyl) benzamide and is listed in Table I above an compound II-1. This compound was made according to scheme I above, starting with 3-nitro-benzoyl chloride and 2,6-dimethyl aniline, and as otherwise described above under the general experimental conditions employed. The 3-amino-N-(2,6-dimethyl phenyl) benzamide had a melting point of 200°–202° C., wave numbers of 1665, 1620cm$^{-1}$, an empirical formula of $C_{15}H_{16}N_2O_1$, a theoretical elemental analysis of C, 74.97% H, 6.71% and N, 11.66%, and an actual elemental analysis of C, 74.87%; H, 6.73% and N, 11.63%.

When evaluated as an anticonvulsant on male Corworth Farms number-one mice in accordance with the pharmacology procedures outlined herein, this compound had a TD 50 value of 284.57 mg/kg, an ED 50 MES value of 13.48 mg/kg and a PI MES value of 21.11.

The term "benzanilide" as used herein, with respect to the compounds of the present invention, means the unsubstituted compound having the structure

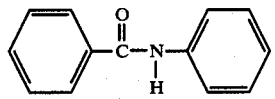

The compounds of the present invention may also be termed benzamides of aniline and substituted anilines.

All of the test data reported herein is based on testing conducted by the Anticonvulsant Drug Development Program, Epilepsy Branch, Neurological Disorders Program, National Institute of Neurological and Communicative Disorders and Stroke. The tests used are described in J. F. Reinhard and J. F. Reinhard, Jr., "Experimental Evaluation of Anticonvulsants", in Anticonvulsants, J. A. Vida, Ed., Academic Press, New York, N.Y., 1977.

U.S. Pat. No. 4,379,165 also contains a description of the various test procedures and related terms that were used as part of such testing activities. The disclosure of U.S. Pat. No. 4,379,165, in this regard, is hereby incorporated herein by reference.

The 3- and 4-amino-N-(alkylphenyl) benzamide compounds of the present invention, and in particular 4-amino-N-(2,6-dimethylphenyl) benzamide, are anticonvulsant agents with a high therapeutic ratio and long half-life, and are therefore useful in the treatment and prevention of convulsions in mammals. In particular, these compounds are effective against tonic extensor seizures elicited by maximal electroshock and should therefore be useful for treating generalized tonic-clonic ("grand mal"), cortical focal, complex partial (temporal lobe epilepsy), simple partial (focal motor), and post-traumatic seizures in humans. This activity is demonstrated in the maximal electroshock induced convulsion inhibition assay which is disclosed herein.

What is claimed is:

1. A method for treating or preventing convulsions in mammals in need of such treatment which comprises administering to said mammal an effective amount of a 3- or 4-amino-N-[(alkyl)$_n$phenyl)]benzamide or a pharmaceutically acceptable acid addition salt thereof, and wherein said alkyl group contains 1 to about 4 carbon atoms and n is 1 or 2.

2. A method as in claim 1 in which said benzamide is a 3- or 4-aminobenzanilide having the structure:

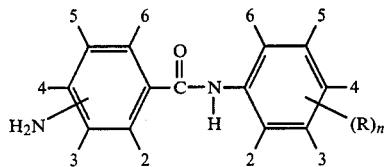

wherein R is a $C_1$ to $C_4$ alkyl group and n is 1 or 2, and the H2n and R groups are positioned as follows in their respective phenyl rings:

| Position of H$_2$N Group in left hand phenyl ring | Position of R groups and H atoms in right hand phenyl ring | | | | |
|---|---|---|---|---|---|
| | 2 | 3 | 4 | 5 | 6 |
| 3 | CH$_3$ | H | H | H | CH$_3$ |
| 4 | CH$_3$ | H | H | H | H |
| 4 | H | CH$_3$ | H | H | H |
| 4 | H | H | CH$_3$ | H | H |
| 4 | CH$_3$ | CH$_3$ | H | H | H |
| 4 | CH$_3$ | H | CH$_3$ | H | H |
| 4 | CH$_3$ | H | H | CH$_3$ | H |
| 4 | CH$_3$ | H | H | H | CH$_3$ |
| 4 | H | CH$_3$ | CH$_3$ | H | H |
| 4 | H | CH$_3$ | H | CH$_3$ | H |
| 4 | CH(CH$_3$)$_2$ | H | H | H | H |
| 4 | CH(CH$_3$)$_2$ | H | H | H | CH$_3$ |
| 4 | CH(CH$_3$)$_2$ | H | H | H | CH$_2$CH$_3$ |

3. A method as in claim 1 in which said benzamide is a 3-amino-N-benzamide.

4. A method as in claim 1 in which said benzamide is a 4-amino-N-benzamide.

5. A method as in claim 4 in which said benzamide is 4-amino-N-(2,6-dimethyl phenyl) benzamide.

* * * * *